(12) United States Patent
Thomas

(10) Patent No.: US 7,336,189 B1
(45) Date of Patent: Feb. 26, 2008

(54) HUMAN LOCATOR SYSTEM AND METHOD

(76) Inventor: Barry W. Thomas, 16316 Woolwine Rd., Charlotte, NC (US) 28278

( * ) Notice: Subject to any disclaimer, the term of this patent is extended or adjusted under 35 U.S.C. 154(b) by 143 days.

(21) Appl. No.: 11/177,612

(22) Filed: Jul. 8, 2005

(51) Int. Cl.
G08B 23/00 (2006.01)

(52) U.S. Cl. ............... 340/573.4; 340/573.1; 340/825.49; 340/539.12; 340/539.13

(58) Field of Classification Search ............ 340/573.1, 340/573.4, 825.49, 539.12, 539.13; 455/404.2; 342/357.07
See application file for complete search history.

(56) References Cited

U.S. PATENT DOCUMENTS

| 3,949,400 | A | * | 4/1976 | Shores | 342/356 |
| 5,519,403 | A | * | 5/1996 | Bickley et al. | 342/352 |
| 5,629,678 | A | * | 5/1997 | Gargano et al. | 340/573.4 |
| 6,317,049 | B1 | * | 11/2001 | Toubia et al. | 340/573.4 |
| 6,437,696 | B1 | * | 8/2002 | Lemelson et al. | 340/573.4 |
| 6,567,044 | B2 | * | 5/2003 | Carroll | 342/465 |
| 6,639,516 | B1 | * | 10/2003 | Copley | 340/573.4 |
| 6,710,713 | B1 | * | 3/2004 | Russo | 340/573.1 |
| 7,187,960 | B2 | * | 3/2007 | Abreu | 600/310 |
| 2002/0070874 | A1 | * | 6/2002 | Williams et al. | 340/825.49 |
| 2005/0186938 | A1 | * | 8/2005 | Hunter | 455/404.2 |
| 2005/0228268 | A1 | * | 10/2005 | Cole | 600/420 |

FOREIGN PATENT DOCUMENTS

DE 2628193 A * 12/1977

* cited by examiner

Primary Examiner—Jeffery Hofsass
Assistant Examiner—Anne V. Lai
(74) Attorney, Agent, or Firm—The Harrington Practice PLLC; James M. Harrington

(57) ABSTRACT

A human locator system and method conducts long-range locating with components or steps that are not readily visible on the person of the lost human, and that is fully independent of external communications and power systems. The human subject is provided with a beacon that may be concealed on or in the body, which is activated to produce a signal which may be sensed by a sensor or receiver deployed to scan a field of search in which the human subject may be located. The beacon indicates a signal origination point that is indicative of the location of the human subject by differentiating the human subject in a pre-arranged manner from the background region in which the human subject is located.

16 Claims, 3 Drawing Sheets

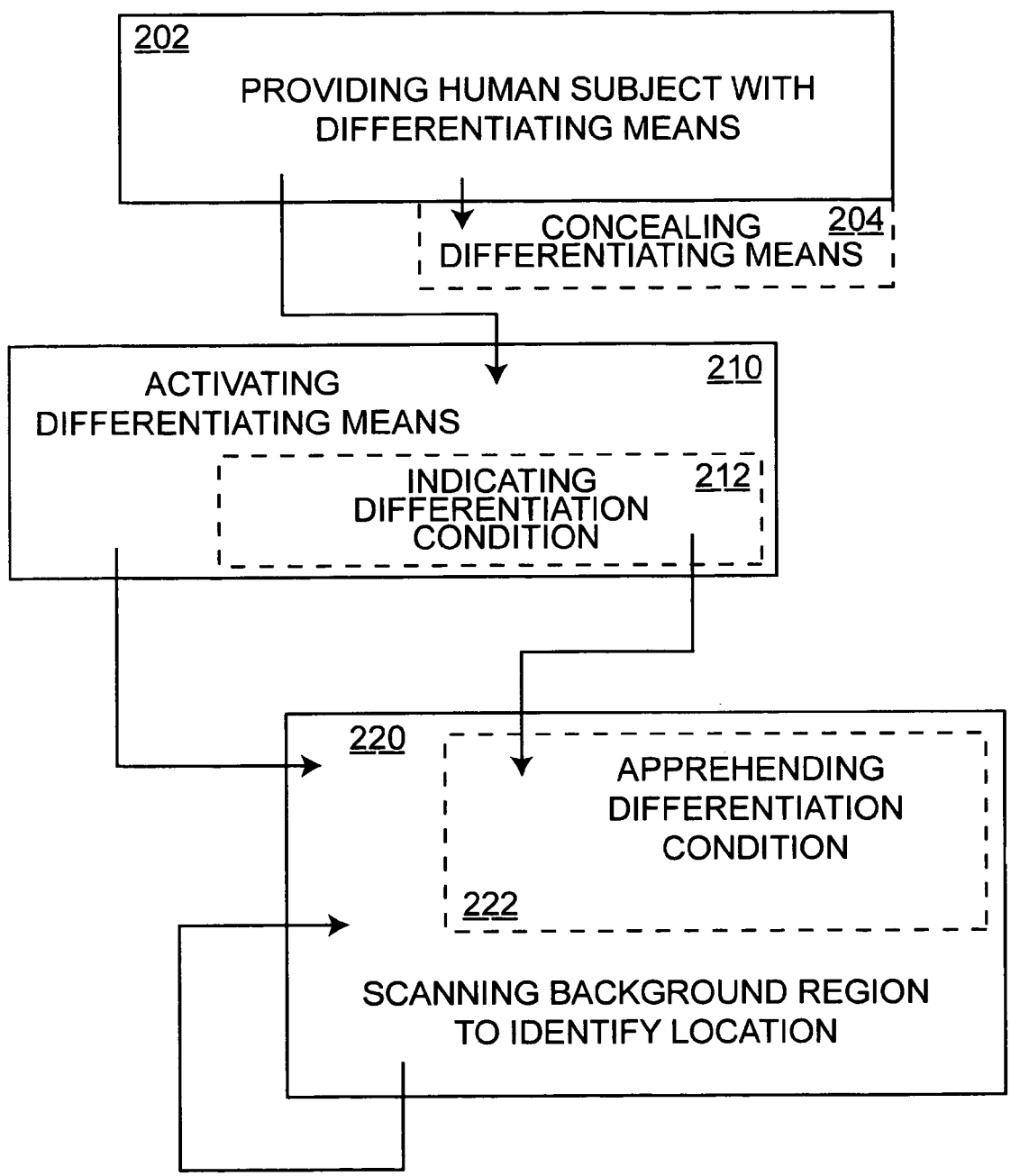

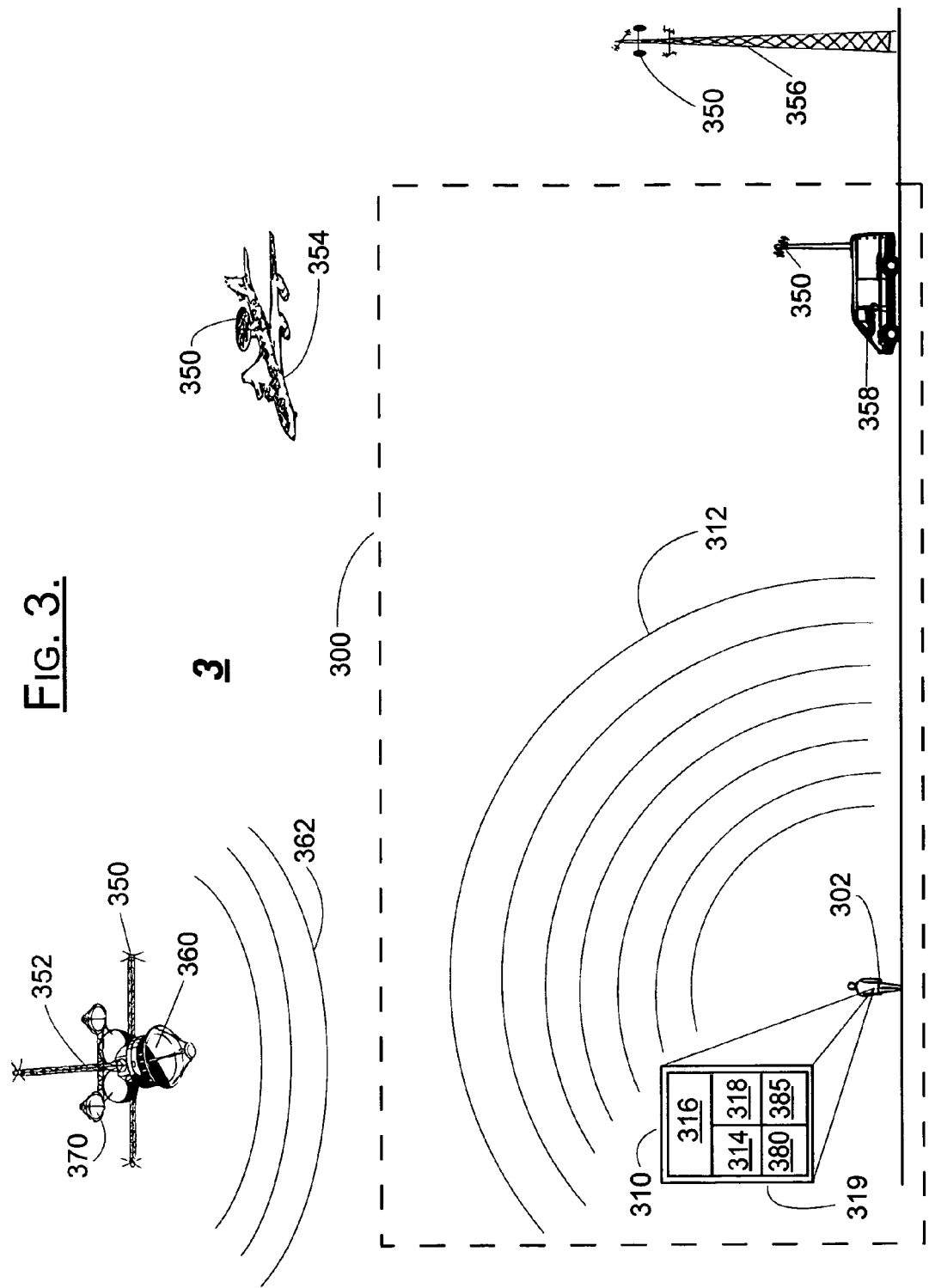

HUMAN LOCATOR SYSTEM AND METHOD

FIELD OF THE INVENTION

The present invention relates to a system and method for locating a lost human, and more specifically to such a system which conducts long-range locating with components or steps that are not readily visible on the person of the lost human, and that is fully independent of external communications and power systems.

BACKGROUND OF THE INVENTION

One of the enduring problems of controlling the movement of humans is that the world is large, and human ability to perceive the location of a human visually is limited by factors inherent in the process of visual acquisition of images. At the outset, it should be noted that control of movement can be either a captivity-promoting or freedom-promoting activity. For example, a person who has been abducted is moved inconsistent with his own control and in accordance with the wishes of his captors, who may secrete him and exercise that control for nefarious purposes. Alternatively, a person who is incarcerated may escape, and the ability of the authorities to return an escapee to custody may be thwarted by the escapee's ability to hide.

Various methods and systems for locating humans have been employed, with varying degrees of success. For centuries, humans have used specially trained dogs to track fugitives and lost persons. Search-and-rescue or search-and-recovery operations make use of aerial photography and visual search techniques to cover wide areas. Criminal investigation, interrogation, and detective work may lead to the acquisition of a human's location. Ankle bracelets may be used to sound an alarm when a confined person leaves the area in which he is confined, although they provide no locating capacity if the confined person leaves the area or removes the bracelet. Particularly in the case of transportation vehicles such as aircraft, boats, and cars, a homing beacon or transponder may be employed to assist in location. Radio or satellite communications may also provide assistance, and in the case of a person who has become lost in the outdoors, the Global Positioning System (GPS) and the wider availability of personal radio, radiotelephone, and satellite communications have contributed to a greater ability to find a person.

However, the systems in use to date all have drawbacks that limit their use in particular situations which have become unfortunately common.

As applied to escapees from prison custody, these systems fail because they can be actively thwarted by the escapee, or because they rely upon some past (but post-escape) location of the escapee to be known to another person, or because they are not cost-effectively nor compulsorily carried by the escapee. As applied to lost persons, these systems fail because of a lack of sufficient electrical power to run them, or because they have become damaged, or because they rely on the lost person to carry them and operate them effectively. As applied to an abducted person, in addition to the problems experienced by a "lost" person, these systems may be discovered actively thwarted by the abductor, or they may not work in sufficient time before the abductor carries out his nefarious purpose, or attempts to use them may cause the abductor to engage in violence to stop them.

In any of these cases, the failure to apprehend the location of the person of interest on a short timetable can have highly negative consequences. A prison escapee may commit additional crimes. A person lost in wilderness may die or be seriously harmed by exposure, starvation, or animal attack or other injury. A person who is abducted may become the victim of an even more serious personal violation, such as rape, torture, or murder. What is needed, then, is a system and method which fulfills at least three criteria necessary to promote the safe recovery of a lost person: (1) capability of identifying the person at a nontrivial distance; (2) undetectability to the naked eye, being concealable within or on the body; and (3) full independence from visible external systems, such as communications devices and power systems.

Various systems have been proposed which fulfill only one or two of these criteria. For example, the state of the art is well acquainted with radio-frequency identification devices (RFIDs), which can be made so small as to be undetectable to the naked eye and fully concealable, and which are independent of any power source. However, RFIDs have an extremely limited range—under present technology, only as much as 100 feet—that is trivial for the purpose to which the present invention is directed, although RFID technology may be useful for the present invention if the range can be extended. Conventional communications devices, such as radios and radiotelephones are capable of providing information at a distance, and can be fully independent, but are not readily concealable on or in the body.

SUMMARY OF THE INVENTION

In accordance with the aforementioned needs, and in elimination of the disadvantages and drawbacks of prior-art systems, the present invention includes a method of locating from a substantial distance a human subject disposed at an unknown location. The method generally includes the steps of providing the human subject with a visually undetectable beacon for generating a signal having as its point of origin the location of the human subject, concealing the beacon on the human subject, activating the beacon to produce an electromagnetic (EM) signal, and repetitively scanning an area to apprehend the signal and identify the location of the human subject.

In another feature of the invention, the step of providing the human subject with a visually undetectable beacon includes the step of providing the human subject with a powered visually undetectable beacon. Various power sources, including chemical batteries, capacitors, kinetic batteries, and fuel cells, may be selected to serve as a power source for the beacon.

The beacon itself will generate an electromagnetic signal, such as a radio signal, a microwave signal, or an infrared signal, which is indicative of a signal origination point. Specifically, the beacon will operate by radiating a signal, whether continuously, or in a periodic fashion, or in response to an activation signal indicating that a scanning device is "listening" for the signal.

In a further feature of the invention, the step of concealing the beacon includes a step for concealing the beacon from ready discovery by persons in the vicinity of the beacon, including the human subject, who are not aware of the beacon's presence. This step for concealing the beacon may include implanting the beacon under the skin of the human subject, inducing the human subject to swallow the beacon, painting or otherwise applying the beacon to the skin or clothing of the human subject, or placing a body-chemistry-altering substance within the body of the human subject in order to generate the beacon through the excretion of body wastes, principally including sweat.

In yet another feature of the invention, the step of activating the beacon includes the step of directing an activation signal pulse across the general area in which the human subject is believed to be located, or potentially located. Additionally, repetitive scans of the area may include the step of apprehending an echo pulse from the beacon.

In still another feature of the invention, the method includes the step of sensing health condition information for the human subject, or using a GPS receiver to identify location information for the human subject, and transmitting the health or location condition information as part of the signal.

While the above portion of the summary of the invention has been directed principally at methods incorporating active electronic transmitters, the present invention may also be more generally described as a method of locating, from a substantial distance, a human subject who is disposed at an unknown location within a background region. The method generally includes the steps of providing the human subject with visually undetectable differentiating means for sensibly differentiating himself from the background region, activating the differentiating means, and repetitively scanning the background region to identify the location of the human subject.

The visually undetectable differentiating means may be powered by a chemical battery, a capacitor, a kinetic battery, a fuel cell, or a similar power source, although some methods of locating the human subject may not require the use of a powered differentiating means.

Consistent with the principle under with the present invention operates, the method includes the step of indicating a differentiation condition for differentiating the human subject from the background region. Ideally, the differentiating means will produce an EM radiation signature which is particularly tuned to characteristics which differ from the EM radiation profile of the background region and any objects located therein. Various EM radiation signatures are possible depending upon the sensing technology used to conduct the step of scanning the background region, without departing from the scope of the present invention.

As noted previously, the differentiating means should be concealed upon the human subject, whether by implantation under the skin, swallowing, painting or otherwise applying the differentiating means to the exterior of the human subject, or placing (as by injection, swallowing, inhaling, or the like) a body-chemistry-altering substance within the body so as to generate a differentiation condition for the human subject through the excretion of body wastes, principally including sweat.

The step of repetitively scanning the background region preferably includes the step of apprehending a differentiation condition signaled by the differentiating means.

The present invention also includes a system for locating a human subject who is disposed at an unknown location. The system includes a beacon for generating a signal having as its point of origin the location of the human subject. The beacon includes a power supply, a transmitter for producing the signal, and a switch for activating the signal. The system further includes at least one sensor for detecting the signal from a substantial distance. The beacon is sized and configured so as to be readily concealed on or within the body of the human subject.

The power supply, as has been noted previously, may be any suitable power source, including by way of example a chemical battery, a kinetic battery, a capacitor, or a fuel cell. The transmitter may be configured to transmit a signal on virtually any frequency on the electromagnetic spectrum, although as a practical matter, being limited by the capacity of the power supply and the tolerance of the human subject for the EM radiation, the range of usable frequencies may be limited primarily to the radio, microwave, and infrared bands.

In another feature of the invention, particularly in connection with an implanted system, the switch may be palpable for actuation from outside the body. Alternatively, the switch may configured to be actuated upon receipt of a signal from outside the body.

The beacon may be concealed upon the body of the human subject in one of the ways previously noted, such as by swallowing by the human subject or by implantation. In the case of a swallowed beacon, the beacon will be preferably configured for operation within the body of the human subject, and may include a shield for protecting the beacon against digestion. Other shielding may be necessary or advisable in the context of an implanted beacon.

A sensor according to the present invention may include means for directing an activation signal pulse across a search area, perhaps in a radar-style sweep of the search area. In such a system, the sensor will also preferably include means for receiving an echo pulse from the beacon, which will be indicative of the location of the beacon and thus the human subject.

The system of the present invention may also include a condition sensor for sensing health condition information for the human subject, or a GPS receiver configured to identify location information for the human subject. The transmitter in such cases will be configured to receive the health condition information or location information and to transmit that information as part of the signal.

BRIEF DESCRIPTION OF THE DRAWINGS

Further features, embodiments, and advantages of the present invention will become apparent from the following detailed description with reference to the drawings, wherein:

FIG. 2 is a flow diagram illustrating an alternative embodiment of a method according to the present invention; and FIG. 3 is a schematic view of a system according to the present invention.

DETAILED DESCRIPTION OF THE PREFERRED EMBODIMENTS

Figure 1:
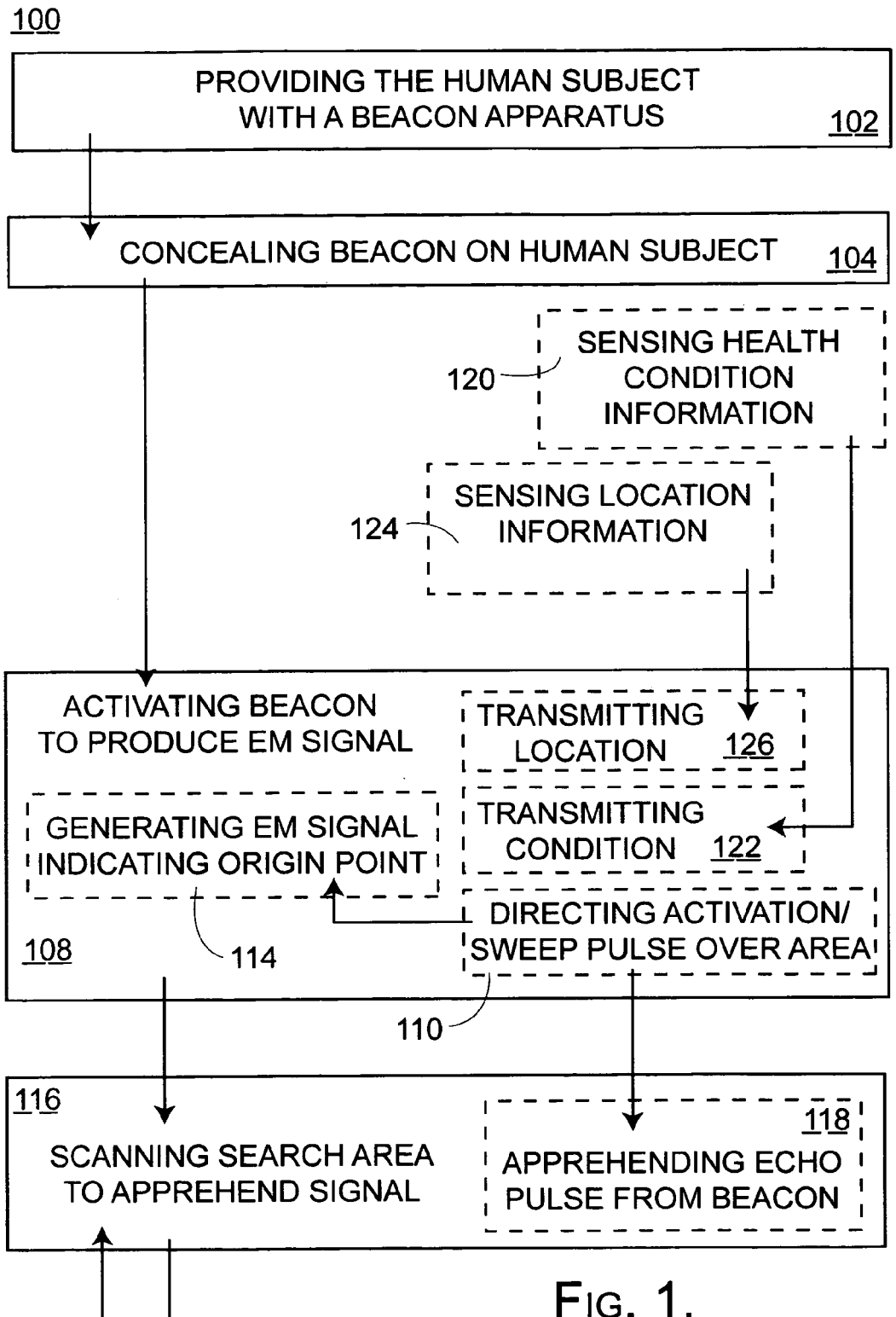
FIG. 1 is a flow diagram illustrating a method according to the present invention.

The present invention includes a method of locating a human subject who is disposed at an unknown location, which includes three principal features or characteristics that differentiate the method of the present invention from prior-art systems and methods. These features include (1) the capability of conducting identification or locating operations at a nontrivial distance; (2) undetectability of the system or method by the naked eye, principally by active concealment of apparatus within or on the body; and (3) full operational independence from visible external systems, such as communications devices and power systems.

At the outset of this detailed description it should be noted that the reasons why these features are critical to the operation of the present invention relate to the general nature of the inability of the interested party to locate the human subject of the search. For example, a person who has been abducted is controlled in his movements by his abductor, under threat of serious bodily harm or death. Such a person may be held at a location unknown to and remote from authorities, and may be harmed for attempting communication through conventional means. Moreover, the person may not have access to conventional communication methods, such as land-based or wireless telephones or radios, or his abductor may remove conventional apparatus from his possession as part of the abduction. In some cases, the person may be unconscious, or in a worst-case scenario, deceased, in which latter case the search operation may be simply for recovery purposes. The need for remote detection is rooted in two factors, one being the need to plan a rescue that preserves surprise, and the other being that even the person's general location may be unknown.

Alternatively, the person whose location is unknown may be an escapee from custody, and may be regarded as physically dangerous, or apt to commit a new crime. Such a person will for obvious reasons not make attempts to contact the authorities to aid them in locating him, nor will he likely carry or use conventional apparatus which may aid in the tracking. Indeed, the entire purpose of a prison escapee's escape is to secrete himself in a location where the authorities will not find him.

In a third scenario, a person who is lost in a wilderness area, for example, or who may lack the mental acuity necessary to return home even in an inhabited area, may not have access to functional means of communication, or may be physically or mentally unable to communicate even if functional means of communication are available. Additionally, while in such a situation it is unnecessary for a locator system to be undetectable to the naked eye per se, the permanent or long-term temporary installation of such a system onto the human body which is attendant to an undetectable system may prove useful.

In any of these situations, the principal activity toward which the present invention is directed is in differentiating the human subject from his surroundings on a long-range basis, in order to identify the location of the human subject within those surroundings. Because these surroundings are of comparatively little interest in a search operation, they may be referred to as "background," or one or more "background regions."

Compared to the earth, the human body is small and easily hidden from view. However, by using portions of the electromagnetic spectrum other than, or in addition to, visible light, particularly on a pre-arranged basis, the contrast between the human subject and the background may be heightened in a manner that results in reliable communication of location information without tipping off persons in the immediate vicinity as to the fact of communication.

It goes without saying that in virtually all scenarios of the type to which the present invention is directed, time is of the essence in locating and recovering the human subject. When a person goes missing, the authority responsible for the search has in most cases a small amount of information from which to proceed. For example, the missing person's identity is known, and his location at some prior point in time is known. Information about the person's habits or health, or information about his abductors (in abduction cases) or plans for and capabilities of movement (in lost persons cases) or modus operandi or favored strategies (in escapee cases) may assist in determining where and how to search, though usually not definitively so. However, the amount of information available may be so small that recovery on a short timetable is unlikely.

Under the auspices of the present invention, additional information of a more significant and concrete nature may be known on a real-time basis, by the anticipated use of the agreed-upon method or system for communicating. Specifically, when the present invention is employed, the authorities will know that the missing person has been provided with a beacon according to the present invention; they will know how that beacon acts to differentiate the human subject from the background, whether by an active electromagnetic signal or a passive one; they will know for how long, at what intervals, and with what range that beacon will operate; and they will know that the beacon will provide information about the human subject's whereabouts perhaps even without the human subject's knowledge or intervention. As a result, locating the human subject quickly, before further harm may befall the human subject or those around him, becomes more likely.

Referring now to the drawings, and especially to FIG. 1, a method 100 of locating, from a substantial distance, a human subject disposed at an unknown location is illustrated in a flow chart. First, at step 102 the human subject must be provided with a beacon apparatus for generating a signal having as its point of origin the location of the human subject. Various types of beacons suitable for use in conjunction with the present invention will be discussed in detail below. In particular, the beacon may be a powered beacon, such that it is provided with a power source, generally for powering a transmitter to dispatch a signal, or the beacon may be non-powered, deriving its communications capability from some physical feature of the beacon. Regardless, the beacon, especially when active, will preferably be visually undetectable when concealed.

Next, at step 104 the beacon is concealed upon the human subject. This may be accomplished in any of a number of different ways, such as by implanting or injecting the beacon under the human subject's skin, or inducing the human subject to swallow the beacon. This latter method may be regarded as useful when power conservation is at a premium, to prevent operation of the beacon before it is needed. For example, a human subject who is stationed in an area in which he is at a high risk for kidnapping, such as in an occupied zone, might carry the beacon on his person, and during the kidnapping might swallow the beacon.

Alternatively, the beacon that consists of an EM-reflective substance might be painted onto the skin or a portion thereof, or if the beacon consists of a generated EM-reflective substance, the human subject might be provided with a pill or similar device that when swallowed would alter the physical chemistry of the human subject's skin, such that an EM-reflective substance is deposited onto the skin via secretions of sweat.

Those skilled in the art to which the present invention relates will recognize that various steps 104 for concealment can be chosen, and as a practical matter, will be chosen based upon the anticipated type of need for locating the human subject. For example, a person who is going on a backpacking trip through the wilderness might take along a different type of beacon than a person who is to be stationed in an occupied zone, and these two might differ from the type of beacon used for a nursing home patient showing symptoms of senility or for an imprisoned criminal. These various situations differ principally in the amount of help that the human subject might give in activating the beacon at a later step and, correspondingly, in the unwillingness or inability of the human subject to carry a beacon for later use.

At step 108, the beacon is activated in order to produce an electromagnetic signal. Optionally this step 108 may cooperate with step 114, generating an electromagnetic signal indicative of a signal origination point. This step is typically characteristic of powered beacons, which utilize stored energy to produce an active electromagnetic signal. Alternatively, activating the beacon at step 108 may include a process in which the beacon is swept with a radiation of a given type, which is then reflected by the beacon to be received by a sensor.

The characteristics of the EM signal produced at step 108 will depend on the apparatus used to carry out the method of the present invention. While in principle this method could be carried out at any frequency in the EM spectrum, the consumption of power to produce the signal, possible health dangers, and the presence of EM noise within the background conspire to reduce the practical range of EM frequencies employed. Signals within the radio, microwave, short-wave, or infrared bands may be employed pragmatically.

At step 116, an area in which the human subject is believed to be, or which is being searched for signs of the human subject, is repetitively scanned in order to apprehend the signal produced at step 108. Once the signal has been apprehended, the location of the human subject may be reliably identified by tracing the path of the signal to its source. Various means for apprehending the signal are available and will be discussed in greater detail below.

In a preferred embodiment, the step 108 of activating the beacon to produce an electromagnetic signal may optionally include the step 110 of directing an activation pulse over the area. This activation pulse will be described in further detail below, but its principal purpose is to activate the beacon, and especially a powered beacon, in order to conserve power output by not causing the consumption of power prior to the need for location services.

When the activation pulse described as part of step 110 is used, the step 116 of repetitively scanning the area may include the step 118 of apprehending an echo pulse from the beacon. In such an arrangement, the activation pulse may be selected to have characteristics, such as a specific frequency or a particular set of modulation techniques, which are unique to the embodiment of the present invention, and the beacon may be configured to repeat or reflect the activation pulse in a similarly characteristic manner, in order to reduce background noise.

A method according to the present invention may include the step 120 of sensing health condition information for the human subject, such as by using health condition sensors connected to the beacon to measure blood pressure, heart rate, blood oxygenation, immune response, or any similar health characteristic, and the step 122 of transmitting that health condition information as part of the EM signal, such as by modulating the signal to indicate information bits coded to reflect a particular health state. Such information may prove useful in determining the urgency of locating the human subject, what situations might be encountered during a rescue, or the like.

Furthermore, a method according to the present invention may include the step 124 of sensing location information for the human subject, such as by using a global positioning system receiver to identify location information for the human subject. The step 126 of transmitting to the location information as part of the electromagnetic signal may be accomplished in much the same manner as described above in connection with the health condition information transmission. Although as a practical matter the precision of sensing the GPS position of the human subject may be severely limited, providing that information to the sensor may help in more quickly identifying the field of search.

Referring now to FIG. 2, an alternative embodiment of a method according to the present invention is illustrated in a flow diagram. A method 200 of locating, from a substantial distance, a human subject who is disposed at an unknown location within a background region includes the step 202 of providing the human subject with a visually undetectable differentiating means for sensibly differentiating himself from the background region. At step 210, the differentiating means is activated. At step 220, the background region is repetitively scanned in order to identify the location of the human subject.

In comparison to the discussion of the previous embodiment, the differentiating means corresponds generically to the beacon so described, but may represent other alternative embodiments of the invention that do not fairly encompass beacons. Consequently, the differentiating means provided at step 202 may be a powered, visually undetectable beacon.

At step 212, which is conducted in conjunction with the step 210 of activating the differentiating means, a differentiation condition for differentiating the human subject from the background region may be indicated. Typically, this will be an EM signal of some sort, whether generated by the differentiating means itself or reflected from an alternative source of a signal.

As noted previously, the differentiating means is optionally concealed at step 204 upon the human subject. This concealment may be accomplished by implanting the differentiating means under skin of the human subject, or by inducing the human subject to swallow the differentiating means, or by painting the human subject with the differentiating means, or by placing a body-chemistry-altering substance in the body of the human subject in order to generate a differentiation condition through excretion of sweat or other body wastes, or by any other suitable step compatible with the operation of the method.

At step 222, as part of the step 220 of repetitively scanning the background region, the differentiation condition signaled by the differentiation means is apprehended in order to identify the location of the human subject.

Conceptually, the field of search may be described as a planar surface of a given area, which is covered on the whole of its surface by a large number of different-colored squares. The object of the exercise is to identify a particular square which corresponds to the location of a lost human subject. However, the sensor being used to search is insufficient to identify the square simply evaluating its contents. In the absence of any pre-arranged schematic indication of the location of an individual square upon that plan, there is no reliable way of determining which square is desired. This is principally a function of the resolution and sensitivity of the sensor, in comparison to the need to distinguish a single square as containing the human subject.

In a method according to the present invention, or using a system according to the present invention, a prearranged indicator is selected, which, conceptually speaking, changes the "color" of the desired square to a specific color which is unlikely to be found elsewhere within the field of search. As a result, a sensor may be tuned to scan for that specific color (or, correspondingly, for particular signal characteristics) which indicates the desired square. Depending upon the application, it may be sufficient to identify the proper location to a resolution of as much as a square mile or more, at least on a "first pass" which narrows the field of search so that less efficient but more effective methods of search may be utilized.

This description is particularly apt when, for example, a charged-coupled device is used to apprehend the location-indicating signal, as will be described in detail below.

Referring now to FIG. 3, a system 3 for locating a human subject 302 disposed at an unknown location within an area such as a field of search 300 is shown in a partially schematic, not-to-scale view. The system 3 includes a beacon 310, which is selected for its capacity to generate a signal 312 that has as its point of origin the location of the human subject. The beacon 310 includes a power supply 314, a transmitter 316 for producing the signal, and a switch 318 for activating the signal.

The system 3 also includes at least one sensor 350 for detecting the signal 312 from a substantial distance. Various possible sensor dispositions are identified in the drawing. For example, the sensor 350 may be mounted upon a satellite 352 in orbit about the earth, or upon an airplane 354 in a manner similar to the Airborne Warning and Control System (AWACS) in use by the U.S. Air Force, NATO, and other military forces. Alternatively, the sensor 350 may be mounted upon an antenna tower 356, or may be ground-based and disposed upon a mobile truck 358. As those skilled in the art will appreciate, the particular sensor disposition will be selected according to the search types for which it will be used, as well as the type and strength of signal to be sensed.

The power supply 314 may take any of several different forms, such as a chemical or kinetic battery or a fuel cell, and is better described according to its function as any suitable device for providing an electrical current to the transmitter 316 at a sufficient power rating to produce the signal 312 at a sensibly strong level.

The transmitter 316 may be designed to transmit on any suitable frequency within the EM spectrum, most typically within the radio, short-wave, microwave, or infrared bands, optionally with modulation by any suitable technique, if desired, and preferably tuned to a frequency suitable to the type of sensor being employed.

Particularly when the beacon 310 is to be implanted into the body of the human subject 302, the need to conserve power is particularly acute, and so the beacon is provided with a switch 318. This switch 318 may be palpable from outside the body without compromising the cloaked nature of the beacon 310, by making the switch small and placing it in a location that is just under the skin of the human subject 302, but easily felt by the human subject 302 and, with a palpating action, actuated to activate the beacon.

Alternatively, the switch 318 may be actuated from outside the body be means of receipt of a signal from outside the body, such as a signal pulse as part of the sweep of the sensor 350 through the search area. This configuration would be used in circumstances under which the human subject 302 would not be expected to cooperate by voluntarily actuating the switch 318.

The beacon 310 may be configured for swallowing by the human subject 302 and for operation within the body of the human subject 302 and would thus be made small enough for this to be accomplished readily. In such cases, the beacon will be preferably provided with a shield 319 for protecting the beacon 318 against digestion in the alimentary canal. Alternatively, the beacon 318 may be implanted.

The sensor 350 may include means 360 for directing an activation signal pulse 362 across the search area 300. In conjunction with that arrangement, the sensor 350 may also include means 370 for receiving an echo pulse 312 from the beacon 310.

A system 3 according to the present invention may also include a condition sensor 380 for sensing health condition information for the human subject 302. In such an embodiment, the transmitter 316 will be configured to receive the health condition information and to transmit the health condition information as part of the signal 312. Similarly, a system 3 according to the present invention may include a GPS receiver 385 that is configured to identify location information for the human subject 302. The transmitter 316 would then be configured to receive the location information and to transmit it as part of the signal 302.

As those skilled in the art to which the present invention relates will recognize, the invention described herein is susceptible of broad application and may be carried out using a wide variety of apparatus and communications techniques, without departing from the scope of the invention. Consequently, it is helpful to discuss a few of the operational considerations to be taken into account when practicing the invention. These considerations typically fall into two categories: those related to the beacon, and those related to the sensor. Some considerations are applicable to both segments.

For example, the maximum operational distance between the beacon and the sensor is a factor that must be considered when designing a particular apparatus for carrying out the locator method of the present invention. When the field of search is large, the maximum operational distance will be large, both because a single sensor must cover the field of search from a given point which is necessarily more distant from some parts of the field than others, and because the larger the field of search, the higher in the sky the sensor must be in order to receive the signal. A field of search that is many square miles in size may require a sensor that is quite distant from the beacon within the human subject.

However, having a more distant sensor necessarily sacrifices resolution and signal strength. An increasingly significant portion of the power of the beacon's signal is lost to atmospheric interference as the distance between beacon and signal increases. Moreover, depending upon the type of sensor used to apprehend the signal, the resolution of the sensor at a larger distance causes the signal to be isolated to a larger sub-area of the field of search.

Correspondingly, the range of the signal varies with the power input to the beacon. For self-contained powered systems, as many of the preferred embodiments are, the amount of power available to the beacon may be rather limited. A person skilled in the art will balance the need to conserve power to maximize the number of opportunities the sensor has to apprehend the beacon signal against the need to produce a signal of sufficient strength and duration to be sensed. The selection of an optimal operational range will depend on the anticipated maximum operational distance and the number of sensors to be deployed, and this may inform the selection of a communication technique.

Of course, various techniques for maximizing the available power are available. The use of next-generation power supplies such as fuel cells may provide more available power than batteries of a similar size, and thus may be preferred. Alternatively, batteries which are designed to recharge themselves by conserving kinetic energy may be preferred for long-term use because they do not depend upon a resource of finite supply to produce power for the beacon. For other applications, chemical batteries such as conventional alkaline, nickel-metal hydride, and lithium-ion batteries might be sufficient. For still other applications, a capacitor may be inductively charged to store energy remotely from available sources, which may be released as needed to power the beacon; this type of arrangement may be indicated when the system is of the "radar" type described above and below.

Additionally, power management techniques are available. A system could employ a timer-controlled switch to activate the beacon only during certain times of day, or for short, discrete periods throughout operation. In fact, this technique might assist in differentiating the beacon from the background by generating a pulse that could be more readily discerned, particularly from noise or false positives, than a continuous source, and in the case of systems with active health condition or location information features, could serve to modulate the signal to transmit that information. Alternatively, the switch could be actuable and de-actuable by the human subject directly, so that the signal could be turned on only when the human subject is in a location where transmitting a sensible signal is possible. The switch could also be actuable by a radio signal emitted for that purpose, so as to turn on beacons in an area to be scanned by the sensor.

Another operational consideration relates to the type of beacon that is selected. The selected beacon will be principally defined by two related factors: first, the frequency at which it operates, and second, the manner in which it produces a signal.

The frequency of operation will be selected to reflect certain operational characteristics such as the maximum operational distance, the possible presence of signal-blocking landscape features such as buildings or geographical features, and the potential exposure of the human subject to harmful radiation. For example, a beacon could use gamma rays in a high effective manner, such as by implanting the human subject with a small amount of fissile material, but the beacon would cause harm to the human subject. For that reason, the frequency is as a practical matter confined to less energetic portions of the EM spectrum, including the radio, short-wave, microwave, and infrared bands. While some harm to the human subject might be tolerated in order to maximize the chances of safe recovery, severe harm is to be avoided, and care should be taken to ensure the operational safety of an implanted beacon.

Additionally, frequencies that require a clear line-of-sight between the beacon and the sensor, or that are typically used for communications of other types (such as wireless telephones, broadcast radio and television, and the like), may be less than effective because the signal may not be clearly differentiated from the background noise.

The manner in which a signal is produced also defines the beacon that is selected. In particular, the ability to produce a sensible signal may be constrained by the maximum available physical footprint of the beacon. Additionally, whether the signal is to be delivered as a beam or in a broadcast fashion may have an impact upon the beacon footprint size and on the design generally.

Other beacons, such as "painted" or "generated" beacons as partially described above, may operate by reflecting radiation of a characteristic frequency in the direction of the sensor. For example, the skin of the human subject may be treated with a substance or induced by an ingested chemical to produce a substance that reflects incident radiation in a manner that is highly differentiated from the background within the frequency band of operation, but that is otherwise invisible within the visible spectrum. Alternatively, the clothing may be treated with such a substance to produce a similar effect.

Yet another operational consideration is related to the type of sensor which is selected to be used. The purpose of this description is not to describe exhaustively the sensors which might be selected, but to describe some of the operational characteristics of the possible sensors generally. The sensor must, of course, be configured to receive the signal from the beacon by "listening" for the type of radiative signal to be produced by the beacon. One basic sensor is a radio receiver which is tuned to the radio frequency at which the beacon is to operate. This is a technique which is well known in the art, and has heretofore been employed in applications such as emergency position-indicating rescue beacons (EPIRBs) of known construction to perform locator services for human subjects and transportation vehicles. It should be noted that these prior-art devices differ from the present invention in that they tend to be rather large and not readily concealed upon or in the human body.

Another type of sensor that may be used as part of the method and system of the present invention is the charge-coupled device (CCD). Devices of this type are well known in the art and are operable to sense incident radiation on selected frequencies. They are typically employed in digital cameras, radiotelescopes, and short-range remote controls and are particularly useful to detect beamed infrared signals. Additionally, because a CCD includes an array of individually acting capacitors, as a practical matter a CCD segments the field of search into a set of smaller sub-fields, which will help to isolate the signal source to a given area even from a great height, such as with a satellite. Conceptually this is similar to pixilation as practiced by a digital camera or radiotelescope, but with each pixel tuned to sense a particular signal from the beacon.

Another emerging technology involves the use of an active pixel sensor (APS), printed using complementary metal oxide semiconductor (CMOS) technology, to advance the "pixilated" concept of segmentation of the field, while incorporating signal conditioning circuitry into the sensor device to refine the sensitivity of the sensor to radiation of a particular frequency. This technique permits the sensor to filter out "noise" more effectively. By contrast, CCDs are more susceptible to noise, and may be required to be chilled to a low temperature to eliminate background sources of radiation.

In view of the aforesaid written description of the present invention, it will be readily understood by those persons skilled in the art that the present invention is susceptible of broad utility and application. Many embodiments and adaptations of the present invention other than those herein described, as well as many variations, modifications, and equivalent arrangements, will be apparent from or reasonably suggested by the present invention and the foregoing description thereof, without departing from the substance or scope of the present invention. Accordingly, while the present invention has been described herein in detail in relation to preferred embodiments, it is to be understood that this disclosure is only illustrative and exemplary of the present invention and is made merely for purposes of providing a full and enabling disclosure of the invention. The foregoing disclosure is not intended nor is to be construed to limit the present invention or otherwise to exclude any such other embodiments, adaptations, variations, modifications and equivalent arrangements, the present invention being limited only by the claims appended hereto and the equivalents thereof.

What is claimed is:

1. A method of locating from a substantial distance a human subject disposed at an unknown location within a background region, the method comprising the steps of:
   providing the human subject with a swallowable device for altering body chemistry of the human subject to generate a beacon for differentiating the human subject within the background region;

concealing the device on the human subject;
activating the device to generate the beacon; and
repetitively scanning the background region to apprehend the beacon by detecting the altered body chemistry and identify the location of the human subject.

2. A method according to claim 1,
wherein the beacon comprises an electromagnetic signal indicative of a signal origination point.

3. A method according to claim 2, wherein the electromagnetic signal is a radio signal.

4. A method according to claim 2, wherein the electromagnetic signal is a microwave signal.

5. A method according to claim 2, wherein the electromagnetic signal is an infrared signal.

6. A method according to claim 2, further comprising the steps of:
sensing health condition information for the human subject; and
transmitting the health condition information as part of the electromagnetic signal.

7. A method according to claim 2, further comprising the steps of:
using a global positioning system receiver to identify location information for the human subject; and
transmitting the location information as part of the electromagnetic signal.

8. A method according to claim 1, wherein the step of activating the beacon includes the step of generating the beacon through excretion of body wastes.

9. A method according to claim 1, wherein the step of repetitively scanning the background region includes the step of apprehending a pulse from the beacon.

10. A method of locating from a substantial distance a human subject disposed at an unknown location within a background region, comprising the steps of:
providing the human subject with visually undetectable differentiating means for sensibly differentiating himself from the background region, comprising a body-chemistry-altering device in order to generate a differentiation beacon through excretion of body wastes;
activating the differentiating means by placing the differentiating means in the body of the human subject; and
repetitively scanning the background region to identify the location of the human subject by detecting the differentiation beacon emanating from body wastes.

11. A method according to claim 10, wherein the step of providing the human subject with a visually undetectable differentiating means includes the step of providing the human subject with a powered body-chemistry-altering device.

12. A method according to claim 11, wherein the powered body-chemistry-altering device includes a power source selected from the group consisting of a chemical battery, a capacitor, a kinetic battery, and a fuel cell.

13. A method according to claim 10, further comprising the step of:
concealing the differentiating means on the human subject.

14. A method according to claim 13, wherein the step of concealing the differentiating means includes the step of inducing the human subject to swallow the differentiating means.

15. A method according to claim 13, wherein the step of activating the differentiating means includes the step of painting the human subject with the differentiating means.

16. A method according to claim 10, wherein the step of repetitively scanning the background region includes the step of apprehending a differentiation condition signaled by the differentiating means.

\* \* \* \* \*